United States Patent [19]

Stache et al.

[11] 4,003,997
[45] Jan. 18, 1977

[54] HEART GLYCOSIDES AND PROCESS FOR PREPARING THEM

[75] Inventors: Ulrich Stache, Hofheim, Taunus; Kurt Radscheit, Kelkheim, Taunus; Werner Fritsch, Neuenhain, Taunus; Werner Haede, Hofheim, Taunus; Ernst Lindner, Frankfurt am Main, all of Germany

[73] Assignee: Hoechst Aktiengesellschaft, Frankfurt am Main, Germany

[22] Filed: Aug. 12, 1974

[21] Appl. No.: 496,892

[30] Foreign Application Priority Data

Aug. 14, 1973 Germany .......................... 2341023

[52] U.S. Cl. .................................. 424/182; 536/7
[51] Int. Cl.$^2$ ........................................ A61K 31/70
[58] Field of Search ............... 260/210.5, 239.55 R; 424/182

[56] References Cited

UNITED STATES PATENTS

| | | | |
|---|---|---|---|
| 3,585,187 | 6/1971 | Heider et al. | 260/210.5 |
| 3,726,857 | 4/1973 | Kubinyi et al. | 260/210.5 |
| 3,741,955 | 6/1973 | Radscheit et al. | 260/210.5 |

*Primary Examiner*—Johnnie R. Brown
*Assistant Examiner*—Cary Owens
*Attorney, Agent, or Firm*—Curtis, Morris & Safford

[57] ABSTRACT

Cyclic 2',3'-ethers of 3-hydroxy-14,15β-oxido-14β-bufa-4,20,22-trienolide, 3β-(α-L-rhamnopyranoside) and process for preparing them. The compounds have a strongly positive inotropic activity and may be used in the therapy of cardiac insufficiency.

8 Claims, No Drawings

HEART GLYCOSIDES AND PROCESS FOR PREPARING THEM

The present invention relates to cyclic 2′,3′-ethers of 3-hydroxy-14,15β-oxido-14β-bufa-4,20,22-trienolide, 3β-(α-L-rhamnopyranoside) of the general formula I

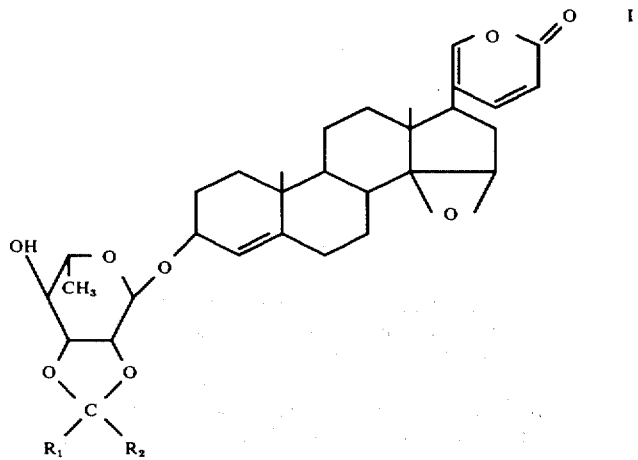

in which $R_1$ and $R_2$, which may be identical or different, each represent hydrogen, an alkyl, aryl or aralkyl group containing 1 to 7 carbon atoms, with the restriction that only one of the two substituents may be hydrogen, or $R_1$ and $R_2$ together represent a linear or branched alkylene group containing 4 to 9 carbon atoms.

The invention furthermore relates to a process for preparing the compounds of the formula I specified above, which comprises reacting in the presence of an acid catalyst, optionally with addition of an inert organic solvent, 3-hydroxy-14,15β-oxido-14β-bufa-4,20,22-trienolide, 3β-(α-L-rhamnopyranoside) with ketones or aldehydes of the general formula II

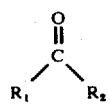

in which $R_1$ and $R_2$ have the meanings given above and/or with the corresponding ketals or acetals of the general formula III

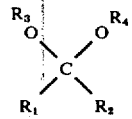

in which $R_1$ and $R_2$ have the meanings given above and $R_3$ and $R_4$, which may be identical or different, represent a lower alkyl group containing 1 to 5 carbon atoms.

The preparation of 2′,3′-ethers of glycosides in which the steroid molecule carries an OH-group in the 14β-position is already known. It is surprising that this process can also be applied to glycosides having a 14,15β-oxido group in the steroid molecule without a splitting of the oxido ring wal formation of a 14β-OH,15α-acid anion derivative and/or without isomerization of the oxido group to a 15-oxo-compound taking place, since this would have to be expected according to Ch. R. Engel, G. Bach, Steroids, 3, 593 to 629 (1966).

The process of the invention proceeds according to the following reaction scheme:

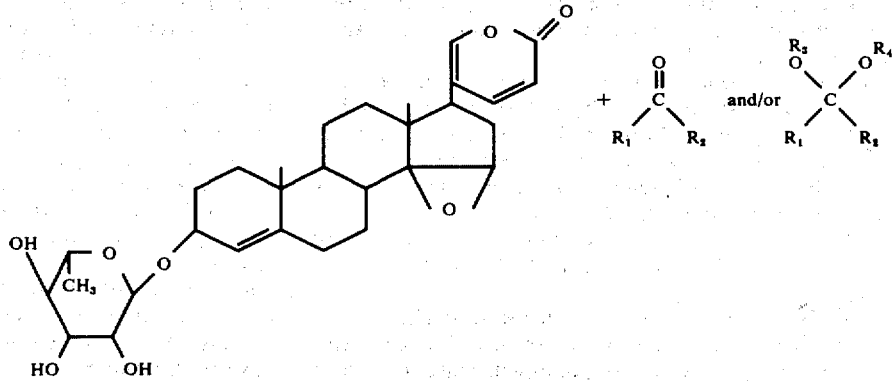

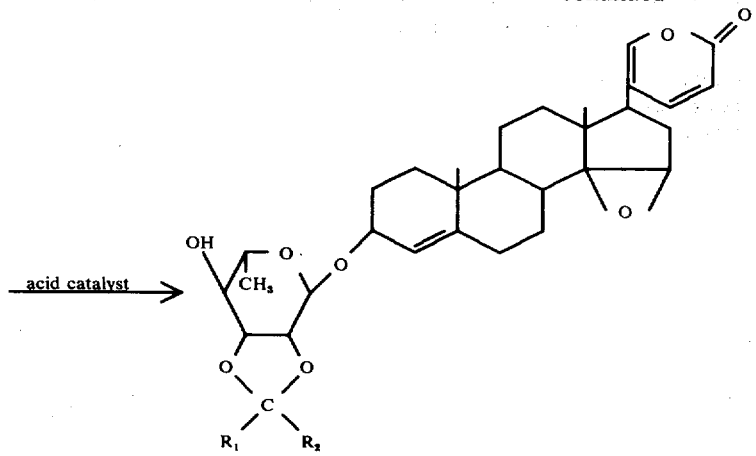

in which $R_1$, $R_2$, $R_3$ and $R_4$ have the meanings given above.

As ketones, there may be used such compounds in which $R_1$ and $R_2$, which may be identical or different, represent alkyl, aryl or aralkyl groups of 1 to 7 carbon atoms, or $R_1$ and $R_2$ together represent a linear or branched alkyl chain of 4 to 9 carbon atoms. Preferably, there are used: acetone, methylethyl ketone, diethyl ketone, dibutyl ketone, dipropyl ketone, cyclopentanone, cyclohexanone, 4-methyl-cyclohexanone, cycloheptanone, cyclooctanone, cyclononanone, cyclodecanone, acetophenone.

As aldehydes, there may be used such compounds in which one of the two radicals $R_1$, $R_2$ is H, whereas the other one represents an alkyl, aryl or aralkyl group of 1 to 7 carbon atoms. Preferably, there are used: acetaldehyde, paraldehyde, benzaldehyde, p-tolylaldehyde, propionaldehyde, butyraldehyde, phenylacetaldehyde.

As ketals or acetals of the aforementioned ketones or aldehydes of the formula III, there are used such compounds in which $R_3$ and $R_4$, which may be identical or different, each represent a lower alkyl group of 1 to 5 carbon atoms, for example methyl, ethyl, propyl, butyl or pentyl. If the ketones or aldehydes are used in admixture with the corresponding ketals or acetals in the reaction, $R_1$ and $R_2$ must have the same meaning.

As acid catalysts, there may be used, for example, mineral or organic acids, sulfonic acid, salts having an acid reaction or acid ion exchangers. There are preferably used: p-toluenesulfonic acid, hydrochloric acid (for example in ether phase), hydrochloric acid, sulfuric acid, phosphoric acid, oxalic acid, formic acid, anhydrous zinc chloride, anhydrous copper sulfate, phosphorylated cellulose preparations, boron-trifluoride etherate, perchloric acid, methane-sulfonic acid, cation exchangers in the H⁺-form.

As inert solvents, insofar as such are used, there are preferably used ethers such as dioxane and tetrahydrofurane, dimethylformamide, dimethyl-sulfoxide, hydrocarbons such as benzene or toluene, or methylene chloride or ethylene chloride, or chloroform or mixtures of the mentioned solvents.

The process of the invention can be carried out in various ways. The following methods are mainly employed:

1. Dissolution or suspension of the steroid in one of the mentioned ketones or aldehydes, if desired with addition of one of the mentioned solvents. After addition of one of the indicated acid catalysts, the reaction mixture is allowed to react for 0.5 hour to 7 days at temperatures between —40° C and the boiling points of the reaction mixtures obtained, preferably at temperatures between 0° and +50° C.
2. By the addition of a ketal or acetal corresponding to the ketone or aldehyde used in the method described under (1), the course of the reaction can be accelerated.
3. Instead of the ketones or aldehydes mentioned in method (1), there may also be used solely the corresponding ketals or acetals, while carrying out the process as described under (1).

In all three cases, working up is effected by neutralizing the reaction mixture with organic or mineral bases after completed of the reaction, which can be determined by thin-layer chromatography, and isolating the reaction products by the usual extraction with organic solvents. By recrystallization from suitable inert organic solvents or by chromatography on silicagel or aluminum oxide, the products of the invention can be obtained in pure form.

The starting compound, i.e. the 3-hydroxy-14,15β-oxido-14β-bufa-4,20,22-trienolide, 3β-(α-L-rhamnopyranoside) can be prepared according to the process described in DT-OS 2 016 704 (German Patent Application laid open to public inspection), by reacting proscillaridin with an acylating agent, treating the acylate obtained with water-separating agents, reacting the Δ 14-olefin obtained with N-halogeno-amides or hypohalic acids, reacting the halahydrin with agents splitting off hydrohalic acids to the expoxide and hydrolyzing the latter to the free L-rhamnoside.

The products of the invention have valuable pharmacological properties. Especially they are distinguished by a strong positively inotropic activity and by a strongly marked action on the heart, as due thereto is shown by animal tests carried out as atrium test, or as K-excretion tests on the isolated heart of guinea pigs. The more favorable ratio of positively inotropic action to cardiotoxicity compared to that of the starting product used in the reaction, must be particularly emphasized, i.e. the products of the invention have a better therapeutic index than the starting compound. Moreover, the products of the invention generally have a significantly higher parenteral resorption rate than the starting compounds.

The products of the invention may be used in the therapy of cardiac diseases, especially for the treatment of cardiac insufficiency. The single dose for a human being may be from about 0.1 to 3 mg per unit. The new compounds may be therapeutically administered above all in their oral application form as dragees, tablets or capsules, for which the usual pharmaceutical carriers, for example, starch, lactose, tragacanth, magnesium stearate and talcum, may be used. For intravenous injections water or physiological sodium chloride solution may serve as solvents.

The following Examples illustrate the invention.

EXAMPLE 1

3-Hydroxy-14,15$_R$-oxido-14$\beta$-bufa-4,20,22-trienolide, 3$\beta$-($\alpha$-L-rhamnopyranosido-2',3'-acetonide)

a. 58 ml of acetone-dimethyl ketal and 581 mg of p-toluenesulfonic acid were added to a solution of 3.44 g of 3-hydroxy-14,15$\beta$-oxido-14$\beta$-bufa-4,20,22-trienolide, 3$\beta$-($\alpha$-L-rhamnopyranoside) in 169 ml of absolute dioxane and 106 ml of acetone. After stirring for 3 hours at 20° C, the reaction mixture was poured into 1 liter of water which contained an excess of NaHCO$_3$. The mixture was extracted exhaustively with methylene chloride. The extracts were washed with water, dried with Na$_2$SO$_4$ and the solvent was removed by distillation under reduced pressure. The foam that remained behind was crystallized from di-isopropyl ether (3.7 g of crystalline product) and re-precipitated from a mixture of methylene chloride and n-hexane. 3.3 g of 3-hydroxy-14,15$\beta$-oxido-14$\beta$-bufa-4,20,22-trienolide, 3$\beta$-($\alpha$-L-rhamnopyranosido-2',3'-acetonide) melting at 213° to 1216° C (Kofler bench) were obtained.

Characteristic infrared bands (KBr): 3470, 1740, 1715, 1630, 1530, 1125, 1070, 1045, 1015, 990 cm$^{-1}$.

Ultraviolet spectrum: $\lambda$ max. = 298 m$\mu$, $\epsilon$ = 5880 (methanol).

b. A solution of 1 g of 3-hydroxy-14,15$\beta$-oxido-14$\beta$-bufa-4,20,22-trienolide, 3$\beta$-($\alpha$-L-rhamnopyranoside) in 60 ml of absolute acetone was combined with 0.8 ml of saturated ethereal hydrochloric acid and stirred for 4 hours at 20° C. The reaction mixture was then poured into 350 ml of water which contained an excess of NaHCO$_3$. After analogous working up and further treatment as described under Example 1 (a), there was obtained the same product with the same data as indicated in said Example.

c. The same product having the same data as those indicated in Example 1 (a) was obtained when proceeding according to Example 1 (b), but using 400 mg of zinc chloride instead of ethereal hydrochloric acid and working up after a reaction time of 3 days.

d. The same product having the same data as those indicated in Example 1 (a) was obtained when proceeding according to Example 1 (b), but using 500 mg of anhydrous copper sulfate instead of ethereal hydrochloric acid and working up after a reaction time of 3 days.

e. A suspension of 1 g of 3-hydroxy-14,15$\beta$-oxido-14$\beta$-bufa-4,20,22-trienolide, 3$\beta$-($\alpha$-L-rhamnopyranoside) in 20 ml of acetone-diethylketal was combined with 1 g of the cation exchanger "Lewatit S 100" (in the H$^+$-form) and stirred for 5 hours at a temperature between 50° and 55° C. The ion exchanger was then removed by suction-filtration and the filtrate obtained was concentrated under reduced pressure. The residue was crystallized and reprecipitated from a mixture of methylene chloride and n-hexane. There was obtained the same product having the same data as those indicated in Example 1 (a).

f. The same product having the same data as those indicated in Example 1 (a) was obtained when proceeding according to Example 1 (b), but using a corresponding amount of 10 N-hydrochloric acid (aqueous) instead of the ethereal hydrochloric acid and working up after a reaction time of 16 hours.

g. The same product having the same data as those indicated in Example 1 (a) was obtained when proceeding according to Example 1 (b), but using 1 g of oxalic acid instead of the ethereal hydrochloric acid and working up after a reaction time of 16 hours.

EXAMPLE 2

3-Hydroxy-14,15$\beta$-oxido-14$\beta$-bufa-4,20,22-trienolide, 3$\beta$-(2',3'-cyclopentylidene-$\alpha$-L-rhamnopyranoside)

a. A solution of 2 g of 3-hydroxy-14,15$\beta$-oxido-14$\beta$-bufa-4,20,22-trienolide, 3$\beta$-($\alpha$-L-rhamnopyranoside) in 150 ml of absolute cyclopentanone was combined with 1.5 ml of saturated ethereal hydrochloric acid and stirred for 6 hours at 20° C. After analogous working up as described in Example 1 (a), 1.7 g of 3-hydroxy-14,15$\beta$-oxido-14$\beta$-bufa-4,20,22-trienolide, 3$\beta$-(2',3'-cyclopentylidene-L-rhamnopyranoside) melting at 148° to 150° C. were obtained.

Characteristic infrared bands (KBr): 3450, 1740, 1720, 1630, 1530, 1120, 1070, 1040, 990 cm$^{-1}$.

Ultraviolet spectrum: $\lambda$ max = 298 m$\mu$; $\epsilon$ = 5750 (methanol).

b. The same product having the same data as those indicated in Example 2 (a) was obtained by combining a suspension of 1,1 g of 3-hydroxy-14,15$\beta$-oxido-14$\beta$-bufa-4,20,22-trienolide, 3$\beta$-($\alpha$-L-rhamnopyranoside) in 60 ml of absolute dioxane and 40 ml of cyclopentanone-dimethyl ketal with 200 mg of p-toluene-sulfonic acid, and, after stirring for 4 hours at 20° C, working up as described under Example 1 (a).

EXAMPLE 3

3-Hydroxy-14,15$\beta$-oxido-14$\beta$-bufa-4,20,22-trienolide, 3$\beta$-(2',3'-cyclohexylidene-$\alpha$-L-rhamnopyranoside)

90 ml of cyclohexanone-dimethyl ketal and 900 mg of p-toluene-sulfonic acid were added to a solution of 2.65 g of 3-hydroxy-14,15$\beta$-oxido-14$\beta$-bufa-4,20,22-trienolide, 3$\beta$-($\alpha$-L-rhamnopyranoside) in 130 ml of absolute dioxane and 81 ml of cyclohexanone. After the whole was stirred for 10 hours at 20° C, working up was effected as described in Example 1 (a). After recrystallization from a mixture of acetone and di-isopropyl ether, there were obtained 1.9 g of 3-hydroxy-14,15$\beta$-oxido-14$\beta$-bufa-4,20,22-trienolide, 3$\beta$-(2',3'-cyclohexylidene-$\alpha$-L-rhamnopyranoside) melting at 142° to 145° C.

Characteristic infrared bands (KBr): 3450, 1740, 1715, 1630, 1530, 1115, 1070, 1040, 1010, 990 cm$^{-1}$.

Ultraviolet spectrum: $\lambda$ max. = 298 m$\mu$, $\epsilon$ = 5450 (methanol).

EXAMPLE 4

3-Hydroxy-14,15$\beta$-oxido-14$\beta$-bufa-4,20,22-trienolide, 3$\beta$-(2',3'-isobutylidene-$\alpha$-L-rhamnopyranoside)

a. A solution of 1 g of 3-hydroxy-14,15$\beta$-oxido-14$\beta$-bufa-4,20,22-trienolide, 3$\beta$-($\alpha$-L-rhamnopyranoside) in 60 ml of methylethyl ketone was combined with 0.8 ml of saturated ethereal hydrochloric acid and stirred for 6 hours at 20° C. Working up was effected subsequently as described in Example 1 (a). After recrystallization from a mixture of methylethyl ketone and diisopropyl ether, there were obtained 740 mg of product melting at 181° to 184° C.

Characteristic infrared bands (KBr): 3440, 1735, 1710, 1620, 1530, 1120, 1065, 1040, 990 cm$^{-1}$.

Ultraviolet spectrum: $\lambda$ max. = 298 m$\mu$, $\epsilon$ = 5650 (methanol).

b. The same product having the same data as those indicated in Example 4 (a) was obtained when proceeding according to Example 4 (a), but using 0.3 ml of concentrated sulfuric acid instead of ethereal hydrochloric acid and working up after a reaction time of 4 hours.

EXAMPLE 5

3-Hydroxy-14,15$\beta$-oxido-14$\beta$-bufa-4,20,22-trienolide, 3$\beta$-(2',3'-ethylidene-$\alpha$-L-rhamnopyranoside)

A solution of 1 g of 3-hydroxy-14,15$\beta$-oxido-14$\beta$-bufa-4,20,22-trienolide, 3$\beta$-($\alpha$-L-rhamnopyranoside) in 50 ml of paraldehyde was combined with 6 g of zinc chloride and allowed to stand for 48 hours at 20° C. After working up as described in Example 1 (a), there were obtained 630 mg of product melting at 170° to 173° C.

We claim:

1. A cyclic 2',3'-ether of 3-hydroxy-14,15$\beta$-oxido-14$\beta$-bufa-4,20,22-trienolide, 3$\beta$-($\alpha$-L-rhamnopyranoside) of the formula

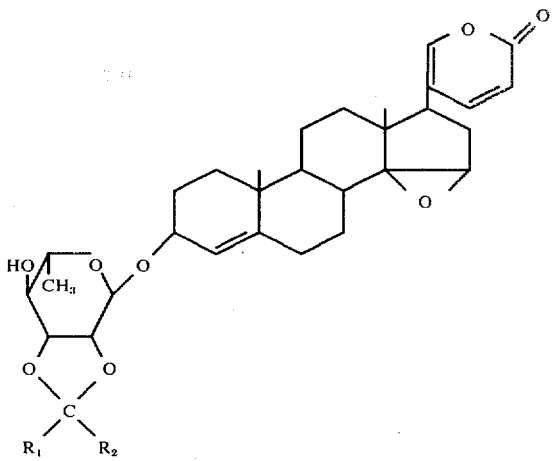

wherein $R_1$ and $R_2$, which may be the same or different but only one of which may be hydrogen, taken alone, are hydrogen, or alkyl, aryl, or aralkyl having 1 to 7 carbon atoms, and $R_1$ and $R_2$, taken together, are linear or branched alkylene having 4 to 9 carbon atoms.

2. 3-Hydroxy-14,15$\beta$-oxido-14$\beta$-bufa-4,20,22-trienolide, 3$\beta$-($\alpha$-L-rhamnopyranoside-2',3'-acetonide).

3. 3-Hydroxy-14,15$\beta$-oxido-14$\beta$-bufa-4,20,22-trienolide, 3$\beta$-(2',3'-cyclopentylidene-$\alpha$-L-rhamnopyranoside).

4. 3-Hydroxy-14,15$\beta$-oxido-14$\beta$-bufa-4,20,22-trienolide, 3$\beta$-(2',3'-cyclohexylidene-$\alpha$-L-rhamnopyranoside).

5. 3-Hydroxy-14,15$\beta$-oxido-14$\beta$-bufa-4,20,22-trienolide, 3$\beta$-(2',3'-isobutylidene-$\alpha$-L-rhamnopyranoside).

6. 3-Hydroxy-14,15$\beta$-oxido-14$\beta$-bufa-4,20,22-trienolide, 3$\beta$-(2', 3'-ethylidene-$\alpha$-L-rhamnopyranoside).

7. A pharmaceutical preparation having cardiac insufficiency activity which comprises an effective amount of a compound as in claim 1 in combination with a pharmaceutical carrier.

8. The method of treating cardiac insufficiency in a patient suffering therefrom which comprises administering an effective amount of a compound as in claim 1.

* * * * *